United States Patent
Kim et al.

(10) Patent No.: US 6,846,934 B2
(45) Date of Patent: Jan. 25, 2005

(54) PHOTOCHROMIC DIARYLETHENE SUBSTITUTED WITH ISOXAZOLE GROUP

(75) Inventors: Eun Kyoung Kim, Yusung-ku (KR); Song Yun Cho, Wonju (KR); Dong Ju Jeon, Yusung-ku (KR); Young Mi Kim, Seo-ku (KR)

(73) Assignee: Korea Research Institute of Chemical Technology, Daejeon (KR)

( * ) Notice: Subject to any disclaimer, the term of this patent is extended or adjusted under 35 U.S.C. 154(b) by 380 days.

(21) Appl. No.: 09/892,655

(22) Filed: Jun. 28, 2001

(65) Prior Publication Data

US 2002/0188043 A1 Dec. 12, 2002

(30) Foreign Application Priority Data

Mar. 6, 2001 (KR) ............................................. 01-11544

(51) Int. Cl.$^7$ .......................... C07D 261/06; B32B 3/00
(52) U.S. Cl. ......................................... 548/247; 428/64
(58) Field of Search ......................................... 548/247

(56) References Cited

U.S. PATENT DOCUMENTS 5,252,371 A    10/1993    Taniguchi et al. ............ 428/64

FOREIGN PATENT DOCUMENTS

| EP | 0488153 | 6/1992 |
|----|---------|--------|
| JP | 3135977 | 6/1991 |
| JP | 4178382 | 6/1991 |
| JP | 3261762 | 11/1991 |
| JP | 3261781 | 11/1991 |
| JP | 3261782 | 11/1991 |
| JP | 4178382 | 6/1992 |
| JP | 4178383 | 6/1992 |
| JP | 5059025 | 3/1993 |
| JP | 5301873 | 11/1993 |
| JP | 6267071 | 9/1994 |
| JP | 7072567 | 3/1995 |
| JP | 7089954 | 4/1995 |
| JP | 8069083 | 3/1996 |
| JP | 9061647 | 3/1997 |
| JP | 9072585 | 3/1997 |
| JP | 9077743 | 3/1997 |
| JP | 9077767 | 3/1997 |
| JP | 9080681 | 3/1997 |

OTHER PUBLICATIONS

Bell, Scott I., "Metalation and Alkylation of 3,6–Dihydrothiazine 1–Oxides Prepared via Diels—Adler Cycloadditions of N–Sulfinyl Dienophils", J. Org. Chem. 1991, 56, 373–377.

Takeshita, Michinori, et al., "Novel saccharide tweezers with a diarylethene photoswitch", Chem. Commun., 1996, 1807–1808.

Irie, Masahiro, "Diarylethenes for Memories and Switches", Chem. Rev. 2000, 100, 1685–1716.

*Primary Examiner*—Kamal Saeed
(74) *Attorney, Agent, or Firm*—Fitzpatrick, Cella, Harper & Scinto (57) ABSTRACT

Novel photochromic diarylethenes substituted with an isoxazole group and the method of preparation are disclosed. Also disclosed are compositions made with the photochromic diarylethenes. The preparation of thin films with the photochromic diarylethenes or compositions thereof are disclosed. The photochromic diarylethenes or compositions thereof may be used, for example in recording materials, photochromic windows, indicating elements, plastic mirrors, photochromic filters, photo switches, photosensitive drums, recording elements, solar cells, lens, fibers and optical elements.

3 Claims, 2 Drawing Sheets

PHOTOCHROMIC DIARYLETHENE SUBSTITUTED WITH ISOXAZOLE GROUP

BACKGROUND OF THE INVENTION

1. Field of the Invention

The present invention relates to photochromic diarylethenes substituted with isoxazole group expressed in the following formula (1), which provide excellent dispersability with polymers, especially fluorinated diacrylate monomers capable of photopolymerization and are capable of giving a thin film, prepared therefrom, of superior photochromic characteristic and high mechanical strength with UV irradiation to be useful as optical recording material and photo switch, (I)

wherein $R^1$ is a direct bond, O, or $C_1-C_3$ alkylene optionally substituted with fluoro; $R^2$ is a hydrogen atom, $(CR^4H)_nOH$ or $C_6(R^5)_mH_1$; $R^3$ is selected from the group consisting of a hydrogen atom, phenylisoxazole, hydroxymethylisoxazole, acetyl, hydroxy, and phenyl; $R^4$ is $C_1-C_{10}$ alkyl; $R^5$ is chloro, nitro, bromo, or the same as $R^4$; X and Y are independently O, N, or S; Z is methylene optionally substituted with fluoro or carbonyl; and n, m and l are an integer of 1 to 5.

2. Related Background Art

Since 1985, diarylethene compounds have been synthesized and known as photochromic compounds having excellent thermal stabilities (Japan Kokai Tokyo Koho; JP 3261781; J. Org. Chem., 1991, 49, 373). Since then, various derivatives have been synthesized and reported for their uses in reversible optical disc, erasable optical disc, photo switch for optical integrated elements, organic photosensitizer, photo-electrode and the like (Japan Kokai Tokyo Koho; JP 789954, JP 8245579; Takeshita, M; Uchida, K; Irie, M. Chem. Commun., 1996, 1807–1808).

Since the diarylethene compounds change their color with UV irradiation and return to the original color with light irradiation having different wavelength, various photochromic compounds are disclosed to be useful in the field requiring for colored state and decolored state (Japan Kokai Tokkyo Koho; JP 5222037, JP 5222035, JP 7242659).

A method for preparing optical recording film by coating with a solution of fluoro-substituted diarylethene compound such as 1,2-bis(2-methylbenzo[b]thiophen-3-yl) hexafluorocyclopentene dissolved with polymer resin has been reported because it has high thermal stability and rapid coloring speed (J. Org. Chem., 1991, 49, 373). However, when this fluorinated diarylethene is dissolved into polymer resin, it has problems in preparation of uniform thin film due to poor dispersability and low photochromic effect for low concentration of fluorinated diarylethene in the resin. On the other hand, when high concentration of the fluorinated diarylethene is used to increase photochromic effect, prepared thin film may be unclear and phase separation can be occured during long storage. Therefore, the conventional photochromic compounds have drawbacks in inferior reliability and storage stability as optical recording materials. Especially, aggregation of conventional diarylethenes results in difficulties in reading and decoding of recorded signals because it gives scattering of data over repeated reversible cycles. In order to solve these problems were disclosed 1-(6'-acetyl-2'-methyl-benzo[b]thiophen-3'-yl)-2-(2"-methyl-benzo[b]thiophen-3"-yl)hexafluorocyclopentene having benzene ring and its derivatives. However, the dispersability is increased some degree but it is hardly regarded as having fully satisfactory sensitivity and photochromic property as photo recording materials (Japan Kokai Tokkyo Koho; JP 05-301873; Irie, M., M. Chem. Rev., 2000, 1685–1716).

SUMMARY OF THE INVENTION

An object of the present invention is to provide a photochromic diarylethene substituted with isoxazole group which can satisfy the aforementioned requirements with better photochromic effect and dispersability with various polymers such as polyolefins and polycarbonates.

Another object of the present invention is to provide a photochromic thin film composition comprising said diarylethene compounds and a method for preparing thin film.

Further object of the present invention is to provide a composition comprising said diarylethene compounds capable for polymerization and a method for preparing thin film, and more particularly, a photochromic thin film composition comprising fluoro-substituted diacrylate monomer capable of photopolymerization and a method for preparing thin film.

DETAILED DESCRIPTION OF THE INVENTION

The present invention is characterized by photochromic diarylethenes substituted with isoxazole group expressed in the following formula (1), (1)

wherein $R^1$ is a direct bond, O, or $C_1$–$C_3$ alkylene optionally substituted with fluoro; $R^2$ is a hydrogen atom, $(CR^4H)_nOH$ or $C_6(R^5)_mH_l$; $R^3$ is selected from the group consisting of a hydrogen atom, phenylisoxazole, hydroxymethylisoxazole, acetyl, hydroxy, and phenyl; $R^4$ is $C_1$–$C_{10}$ alkyl; $R^5$ is chloro, nitro, bromo, or the same as $R^4$; X and Y are independently O, N, or S; Z is methylene optionally substituted with fluoro or carbonyl; and n, m and l are an integer of 1 to 5.

Said compound (1) is prepared by the following process:
1) formylation of the diarylethene compound of formula (2);
2) sequential reaction with $NH_2OH$—HCl and aqueous basic solution and further reaction with N-chlorosuccimide (NCS); and
3) reaction with acetylene compound substituted with $R^2$ in the presence of base catalyst,

(2)

wherein $R^1$ is a direct bond, O or $C_1$–$C_3$ alkylene optionally substituted with fluoro; $R^3$ is selected from the group consisting of a hydrogen atom, phenylisoxazole, hydroxymethylisoxazole, acetyl, hydroxy, and phenyl; X and Y are independently O, N, or S; and Z is methylene optionally substituted with a fluoro atom or carbonyl.

Photochromic compositions containing the diarylethene compound of the present invention include photochromic thin film composition and photochromic thin film composition capable of photopolymerization or thermalpolymerization.

Photochromic thin film composition of the present invention comprises 0.1–90 wt. % of the compound (1), 10–89.9 wt. % of one or more resin selected from the group consisting of polyolefin, polycarbonate, polymethylmethacrylate, polyester, polyvinyl alcohol, polyurethane, and polyimide, and 10–89.9 wt. % of one or more solvent.

Photochromic thin film composition capable of photopolymerization or thermalpolymerization of the present invention comprises 0.1–90 wt. % of the compound (1), 10–99.8 wt. % of fluorinated diacrylate monomer of formula (3), 0–80 wt. % of monomer or oligomer having unsaturated group, 0.1–10 wt. % of initiator of polymerization selected from initiator of thermalpolymerization and initiator of photopolymerization, and 0–90 wt. % of one or more solvent, (3)

wherein n is an integer of 0 to 10.

The diarylethene compound of formula (1) which provides excellent photochromic effect and dispersability with various polymers is prepared by the following method. The preparing method which comprises formylation of diarylethene substituted with $R^3$ of formula (2), conversion to the corresponding N-oxime and reaction with acetylene compound substituted with $R^2$ is shown in Scheme 1.

Scheme 1

1) Said formulation of the diarylethene compound of formula (2) is carried by the known method (Irie, M.; Miyatake, O.; Uchida, K.; Eriguchi, T., *J. Amer. Chem. Soc.*, 1994, 9894).
2) Said oximization is carried by reacting the reactant dissolved in dimethyl foramide with $NH_2OH$—HCl and aqueous basic solution and further reacting with N-chlorosuccimide (NCS) to yield N-oxime compound.
3) Further reaction is carried by reacting with acetylene compound substituted with $R^2$ in the presence of base catalyst in methylene chloride at a temperature of from −10 to 30° C. for from 5 min to 10 hrs. Triethylamine is used as the base catalyst and other reaction conditions such as solvent, temperature, time and purification method can be adjusted depends on the compounds. The obtained diarylethene compounds are identified with NMR, IR and the like.

The composition containing the diarylethene compound of the present invention is particularly described as set forth hereunder.

The photochromic thin film composition is prepared by stirring a mixture comprising 0.1–90 wt. % of one or more compound selected from the compound (1), 10–89.9 wt. % of one or more resin selected from the group consisting of polyolefin, polycarbonate, polymethylmethacrylate, polyester, polyvinyl alcohol, polyurethane, and polyimide, and 10–89.9 wt. % of one or more solvent at 15–130° C.

The organic solvent is selected from acetone, hexane, acetonitrile, $C_1$–$C_{10}$ alcohol, dimethylformamide, tetraalkoxysilane, trialkoxysiliane, dialkoxysilane, sulfuric acid, hydrochloric acid, organic acid, dimethylsulfoxide, pyridine, N-methylpyrrolidinone (NMP), sulfolane, α-methylnaphthalene, methoxynaphthalene, chloronaphthalene, diphenylethane, ethylene glycol, quinoline, dichloromethane, dichlorobenzene, dichlorotoluene, propylene carbonate, xylene, methyl ethyl ketone, chloroform, methylene chloride, trichloroethane, trichloroethylene, tetrahydrofuran, 1,4-dioxane and water.

Other additives, used by one having ordinary skill in the art, such as a retardant, a thickener, an anti-oxidant, and a UV protecting agent may be arbitrarily incorporated in an appropriate content not to obstruct the above-mentioned object of the present invention. The thin film is prepared by molding the composition of the present invention to yield photochromic forming, coating the photochromic forming on the substrate such as silicon wafer and glass by means of spray, dip coating or spin coating, and evaporating solvent at 15–130° C.

The obtained thin film has excellent absorbance in the range of wavelength of 200–500 nm. Further, when Sun light or UV light is exposed to the thin film, diarylethene thin film having excellent absorbance in the range of 300–800 nm is produced.

The diarylethene compound of the present invention provides excellent dispersability with thermalpolymerizable composition or photopolymerizable composition having unsaturated compounds. And further, the diarylethene compound has advantages in excellent dispersability with fluorinated unsaturated monomer, absorbance at 200–800 nm, and photochromic effect, so that it can be useful in indicating materials, optical integrated elements, various sensors, recording materials and optical materials.

Photochromic thin film composition capable of photopolymerization or thermalpolymerization of the present invention comprises 0.1–90 wt. % of one or more selected from the compound (1), 10–99.8 wt. % of fluorinated diacrylate monomer of formula (3), 0–80 wt. % of monomer or oligomer having unsaturated group, 0.1–10 wt. % of one or more polymerization initiator selected from thermalpolymerization initiator or photopolymerization initiator, and 0–90 wt. % of one or more solvent. Examples of monomer having unsaturated group include methyl methacrylate, butyl methacrylate, styrene, and α-methylstyrene. Examples of polymerization initiator include thermalpolymerization initiator such as benzoyl peroxide, 2,2'-azobisisobutyronitrile, and bis(1,1-dimethylethyl)peroxide, and photopolymerization initiator such as 1-hydroxycyclohexyl phenyl ketone, benzophenone, 2-hydroxy-1-[4-(hydroxyethoxy)phenyl]-2-methylpropanone, 2,2-dimethoxy-2-phenylacetophenone, fluorinated diaryltitanocine, and 2,2-bis(hydroxymethyl) propionic acid. Other additives, used by one having ordinary skill in the art, such as a retardant, a thickener, an antioxidant, and a UV protecting agent may be arbitrarily incorporated, if necessary. The thin film is prepared by molding the composition to yield photochromic forming, coating the photochromic forming on the substrate such as silicon wafer and glass, and evaporating solvent at 15–130° C. or irradiating UV light.

The compound of formula (1) or photochromic thin film composition is coated on the substrate selected from conducting electrode substrate such as aluminum foil, aluminum drum, aluminum plate, platinum, Myler film, copper plate, conducting glass and conducting plastic; or a substrate such as polypropylene, propylene carbonate, polymethylmethacrylate, polyurethane, plastic, and glass to form diarylethene thin film which can be used for optical recording materials, photochromic window, indicating elements, plastic mirror, photochromic filter, photo switch, photosensitive drum, recording elements, solar cell, lens, fiber, or optical elements.

Although the present invention is described in detail, it is clearly understood that the same is by way of illustration and example only and is not to be taken by way of limitation of the scope of the present invention.

EXAMPLE 1

Preparation of 1-(6'-oxymoyl-2'-methylbenzo[b]thiophen-3'-yl)-2-(2"-methylbenzo[b]thiophen-3"-yl) hexafluorocyclopentene (OMBTF6)

1-(6'-formyl-2'-methylbenzo[b]thiophen-3'-yl)-2-(2"-methylbenzo[b]thiophen-3"-yl)hexafluorocyclopentene (FMBTF6) (3 g) was dissolved in 50 mL of ethanol. $NH_2OH$—HCl (0.63 g) was added and the mixture solution was stirred for 10 min. NaOH (0.36 g) dissolved in 1 mL of water was dropped into the mixture. After the reaction was completed, the reaction mixture was extracted with methylene chloride. The combined organic layer was dried over $MgSO_4$, and evaporated in vacu to dryness. The crude product was purified by Flash chromatography (ethylacetate/hexane=1/7) to obtain the desired product, OMBTF6(2.0 g,65%).

$^1$H NMR (200 MHz, $CDCl_3$)δ 1.73 (s, 1H), 2.21 (s, 3H), 2.49 (s, 3H), 7.17–7.45 (m, 2H), 7.54–7.83 (m, 5H), 8.20 (s, 1H);

MS m/z 511 (M+, 100), 493 (18), 478 (5), 464 (26), 419 (10)

EXAMPLE 2

Preparation of 1-(6'-chloro-oxymoyl-2',2'-methylbenzo[b]thiophen-3'-yl)-2-(2"-methylbenzo[b]thiophen-3"-yl) hexafluorocyclopentene (COMBTF6)

OMBTF6(1.3 g) prepared in Example 1 was dissolved in 30 mL of DMF and cooled to 0° C. N-chlorosuccinimide (0.51 g) was dropped slowly to the reaction mixture. The reaction mixture was left to room temperature and then extracted with methylene chloride. The combined organic layer was washed with NaCl solution, dried over $MgSO_4$, and evaporated in vacu to dryness to obtain the product, COMBTF6(1.26 g, 91%).

EXAMPLE 3

Preparation of 1-(6'-(5-hydroxymethylisoxazol)-2'-methylbenzo[b]thiophen-3'-yl)-2-(2"-methylbenzo[b]thiophen-3'-yl)hexafluorocyclopentene (IMBTF6)

CMBTF6(1.26 g) prepared in Example 2 is dissolved in 20 mL of methylene chloride and cooled to 0° C. Propargyl alcohol (0.26 g) was added and then triethylamine (0.47 g) was dropped slowly to the reaction solution. The reaction mixture was left to room temperature and then extracted with methylene chloride. The combined organic layer was washed with NaCl solution, dried over $MgSO_4$, and evaporated in vacu to dryness. The crude product was purified by Flash chromatography (ethylacetate/hexane=1/5) to obtain the product, IMBTF6 (74%).

$^1$H NMR (200 MHz, $CDCl_3$) δ 1.70 (s, 1H), 2.23 (s, 1H), 2.50 (s, 1H), 4.84 (s, 2H), 6.60 (s, 1H), 7.16–7.41 (m, 2H), 7.50–7.83 (m, 4H), 8.12 (s, 1H);

MS m/z 565 (M+, 100), 550 (6), 534 (25), 506 (9), 495 (3)

EXAMPLE 4

Preparation of 1-(6'-(5-phenylisoxazol)-2'-methylbenzo[b]thiophen-3'-yl)-2-(2"-methylbenzo[b]thiophen-3'-yl) hexafluorocyclopentene (PIMBTF6)

COMBTF6(2.57 g) prepared in Example 3 was dissolved in 40 mL of methylene chloride and cooled to 0° C. Phenylacetylene (0.96 g) was added and then triethylamine (0.95) was dropped slowly to the reaction solution. The reaction mixture was left to room temperature and then extracted with methylene chloride. The combined organic layer was washed with NaCl solution, dried over $MgSO_4$, and evaporated in vacu to dryness. The crude product (85%) was purified by Flash chromatography (ethylacetate/hexane=4/1) to obtain the colorless product, PIMBTF6.

$^1$H NMR (200 MHz, CDCl$_3$) δ 2.24 (s, 3H), 2.52 (s, 3H), 3.07 (s, 1H), 7.19–7.90 (m, 11H), 8.20 (s, 1H);

MS m/z 611 (M+, 44), 582 (2), 549 (4), 512 (33), 493 (71).

EXAMPLE 5
Preparation of di(6'-phenylisoxazol-2'-methylbenzo[b] thiophen-3'-yl)hexafluorocyclopentene (DPIMBTF6)

According to Example 1, di(6'-formyl-2'-methylbenzo[b] thiophen-3'-yl)hexafluorocyclopentene) (3 g) was dissolved in 50 mL of ethanol. NH$_2$OH.HCl (1.33 g) was added and stirred for 20 min. NaOH (0.7 g) dissolved in 2 mL of water was dropped slowly to the reaction mixture. After the reaction was completed, the reaction mixture was extracted with methylene chloride. The combined organic layer was dried over MgSO$_4$, and evaporated in vacu to dryness. The obtained compound was carried with the same procedure of Examples 2–4 to yield DPIMBTF6 (70%).

$^1$H NMR (200 MHz, CDCl$_3$) δ 1.73 (s, 1H), 2.21 (s, 3H), 2.49 (s, 3H), 7.17–7.45 (m, 2H), 7.54–7.83 (m, 5H), 8.20 (s, 1H).

PREPARATION EXAMPLE 1
Preparation of Fluorinated Diacrylate Monomer (TEBDA)

To tetrafluoro-1,4-butandiol (1.00 g) dissolved in 50 mL of methylene chloride was dropped triethylamine (1.87 g) dissolved in 10 mL of methylene chloride at 6° C. for 10 min while stirring. Acryloylchloride (1.68 g) dissolved in 10 mL of methylene chloride was dropped to the reaction mixture for 15 min. The reaction temperature was raised to room temperature and stirred for 12 hrs. The reaction mixture was washed with saturated NaHCO$_3$ solution and distilled water (×3), dried over anhydrous MgSO$_4$, and evaporated to yield TFBDA (90%). The crude product was purified by column chromatography (ethylacetate/hexane=1:10) to give colorless liquid.

IR(KBr) 1174, 1636, 1745, 2973 cm$^{-1}$;
$^1$H NMR (CDCl$_3$) 4.83 (m, 4H), 6.13–6.73(m, 6H);
$^{13}$C NMR (CDCl$_3$) 59.8, 127.2, 133.2, 164.9;
MS m/z 270.

EXAMPLES 6–7 AND COMPARATIVE EXAMPLES 1–4
Preparation of Photochromic Thin Film Composition Solubilities of diarylethene compounds of the present invention and known diarylethene compounds were compared by dispersing in polycarbonate (PC) solution or fluorinated polyethylene.

Compared diarylethene compounds are 1-(6'-(5-phenylisoxazol) 2'-methylbenzo[b]thiophen-3'-yl)-2-(2"-methylbenzo[b]thiophen-3'-yl)hexafluorocyclopentene (PIMBTF6) prepared in Example 4 and 1,2-bis(2-methylbenzo[b]thiophen-3'-yl)hexafluorocyclopentene (BTF6) and 1-(6'-acetyl-2'-methylbenzo[b]thiophen-3'-yl)-2-(2"-methylbenzo[b]thiophen-3'-yl)hexafluorocyclopentene (AMBTF6) which are disclosed. Each thin film composition was prepared by dissolving 0.03 g (10 wt. %) of diarylethene compound and 0.27 g (90 wt. %) of polycarbonate (PC) or fluorinated polyethylene in a mixture of 1.2 g of chloroform and 1.2 g of trichloroethylene and stirring at room temperature for 6 hrs. The dispersabilities thereof were summarized in table 1.

TABLE 1

| Category | | Diarylethene compound | Polymer | Solvent | Dispersability* |
|---|---|---|---|---|---|
| Exam. | 6 | PIMBTF6 | Polycarbonate (PC) | Chloroform + trichloroethylene | ○ |
| | 7 | PIMBTF6 | **Fluorinated polyethylene | Chloroform + trichloroethylene | Δ |
| Comp. Exam. | 1 | BTF6 | Polycarbonate (PC) | Chloroform + trichloroethylene | ○ |
| | 2 | AMBTF6 | Polycarbonate (PC) | Chloroform + trichloroethylene | X |
| | 3 | BTF6 | **Fluorinated polyethylene | Chloroform + trichloroethylene | X |
| | 4 | AMBTF6 | **Fluorinated polyethylene | Chloroform + trichloroethylene | X |

*Dispersability: ○ = clear solution at RT; Δ = medium solubility; X = insoluble, phase separation and unclear solution
**Fluorinated polyethylene: Xeonex 480, SamYang Corporation EXAMPLES 8~10 & COMPARATIVE EXAMPLES 5~9
Preparation of Photochromic Thin Film Composition Capable of Polymerization Solubilities of diarylethene compounds of the present invention and known diarylethene compounds were compared by dispersing in fluorinated diacrylate monomer (TFBDA) or THF.

The same diarylethene compounds used in Examples 6–7 and Comparative Examples 1–4 are used to obtain the desired composition. Each thin film composition was prepared by dissolving 0.01 g (10 wt. %) of diarylethene compound and 0.002 g (2 wt. %) of 1-hydroxycyclohexyl phenyl ketone as photopolymerization initiator in 0.088 g (88 wt. %) of TFBDA and stirring at room temperature for 30 min. The dispersabilities thereof were summarized in table 2.

TABLE 2

| Category | | Diarylethene compound | Solvent | Dispersability* |
|---|---|---|---|---|
| Exam. | 8 | PIMBTF6 | TFBDA | ○ |
| | 9 | DPIMBTF6 | TFBDA | ○ |
| | 10 | PIMBTF6 | THF | ○ |
| Comp. Exam. | 5 | BTF6 | TFBDA | X |
| | 6 | AMBTF6 | TFBDA | Δ |
| | 7 | IMBTF6 | TFBDA | X |

TABLE 2-continued

| Category | | Diarylethene compound | Solvent | Dispersability* |
|---|---|---|---|---|
| | 8 | AMBTF6 | THF | ○ |
| | 9 | IMBTF6 | THF | ○ |

Figure 1:
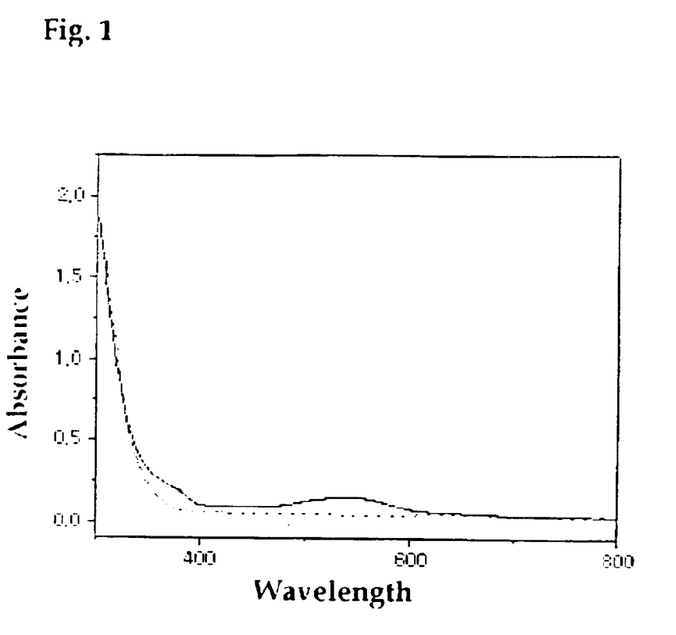
FIG. 1 illustrates optical change in absorption spectra when light with 365 nm of wavelength is irradiated to the polycarbonate photochromic thin film dispersed with the diarylethene compound according to Example 11 of the present invention.

*Dispersability: ○ = clear solution at RT; Δ = medium solubility; X = insoluble, phase separation and unclear solution EXAMPLE 11
Preparation of Thin Film Using Photochromic Thin Film Composition The photochromic composition obtained in Example 6 was filtered through 0.45 micron filter of syringe and filtrate was coated on the surface of glass by using bar code. The coated glass was dried in the vacuum oven at 50° C. for 12 hrs to yield transparent thin film having excellent adhesive and high strength. When the obtained thin film was irradiated with light of over 300 nm, the color was changed to red and then kept in the dark room to remain red color. FIG. 1 illustrates changes of absorption spectra when light with 365 nm of wavelength is irradiated to the photochromic thin film dispersed with the PIMBTF6, wherein a broken line is absorption spectra prior to light irradiation and a solid line is absorption spectra after 5 min from light irradiation.

COMPARATIVE EXAMPLES 10–11
Preparation of Thin Film Using Photochromic Thin Film Composition Photochromic thin films of Comparative Examples 10 and 11 were prepared by using the compositions prepared in Comparative Examples 1 and 2 according to Example 11.

EXAMPLES 12–13
Preparation of Thin Film Using Photochromic Thin Film Composition Capable of Polymerization (Photocuring)

Figure 2:
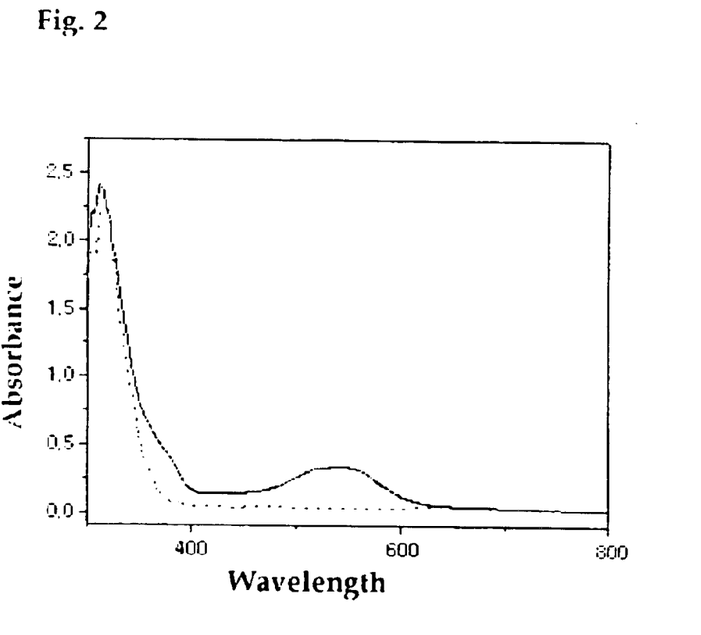
FIG. 2 illustrates optical change in absorption spectra when light with 365 nm of wavelength is irradiated to the photo-crosslinked acrylate photochromic thin film dispersed with the diarylethene compound according to Example 12 of the present invention.

The photochromic compositions obtained in Examples 8 and 9 were filtered through 0.45 micron filter of syringe. Filtrate was injected in between glasses and exposed with UV light for 10 min. One of glasses was removed to yield transparent thin film having excellent adhesive and high strength. When the obtained thin film was irradiated with light of over 300 nm, the color was changed to red and then kept in the dark room to remain red color. FIG. 2 illustrates changes of absorption spectra when light with 365 nm of wavelength is irradiated to the photochromic thin film of Example 12, wherein a broken line is absorption spectra prior to light irradiation and a solid line is absorption spectra after 5 min from light irradiation.

COMPARATIVE EXAMPLE 12
Preparation of Thin Film Using Photochromic Thin Film Composition Capable of Polymerization (Photocuring)

Photochromic thin film was prepared by using the composition prepared in Comparative Examples 6, according to Example 12.

EXAMPLES 14–15
Preparation of Thin Film Using Photochromic Thin Film Composition Capable of Polymerization (Thermal Curing)

Figure 3:
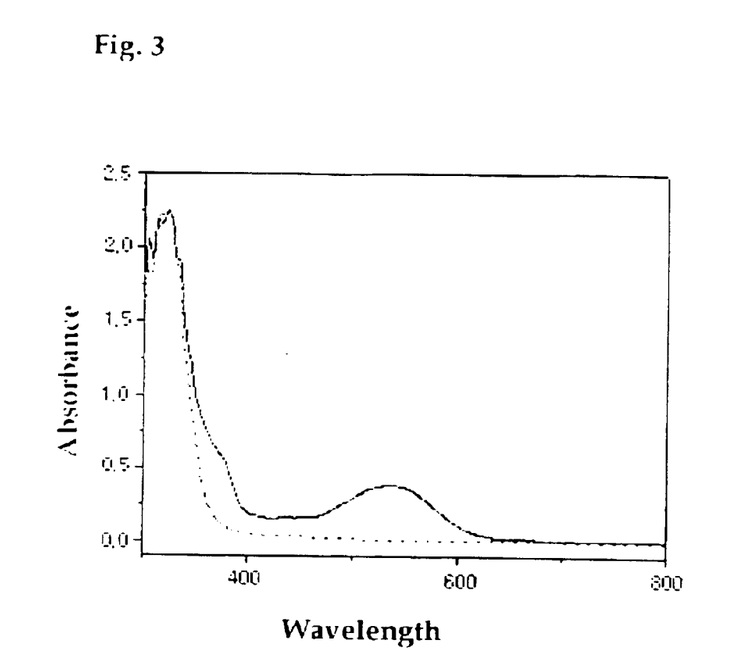
FIG. 3 illustrates optical change in absorption spectra when light with 365 nm of wavelength is irradiated to the thermally crosslinked acrylate photochromic thin film dispersed with the diarylethene compound according to Example 14 of the present invention.

The thin films were prepared according to Example 12 except with thermal curing at 80° C. instead of radiation curing. When the obtained thin film was irradiated with light of over 300 nm, the color was changed to red and then kept in the dark room to remain red color. FIG. 3 illustrates changes of absorption spectra when light with 365 nm of wavelength is irradiated to the photochromic thin film of Example 14, wherein a broken line is absorption spectra prior to light irradiation and a solid line is absorption spectra after 5 min from light irradiation.

COMPARATIVE EXAMPLE 13
Preparation of Thin Film Using Photochromic Thin Film Composition Capable of Polymerization (Thermal Curing)

Photochromic thin film was prepared by using the composition prepared in Comparative Examples 6, according to Example 14.

EXPERIMENTAL EXAMPLE 1
Comparison of Photochromic Characteristics of Thin Films Prepared with Photochromic Thin Film Compositions Photochromic characteristics of the thin films prepared in Example 11 and Comparative Examples 10–11 were summarized in table 3.

TABLE 3

| Category | | Photochromic composition | Substituent of diarylethene | | Content (wt %) | Thickness of film (μm) | $\lambda_{max}$ | Δ OD* $(cm^{-1})$ |
|---|---|---|---|---|---|---|---|---|
| Exam. | 10 | Exam. 6 | —H | (isoxazole-phenyl group) | 10 | 5 | 540 | 235 |
| Comp. Exam. | 11 | Comp. Exam 1 | —H | —H | 10 | 3 | 526 | 148 |
| Exam. | 11 | Comp Exam. 2 | —H | —C(=O)CH$_3$ | 10 | 5 | 539 | 174 |

Δ OD* is an amended value with the thickness of thin film for the difference between absorbance of $\lambda_{max}$ before and after UV irradiation.

EXPERIMENTAL EXAMPLE 2

Comparison of Photochromic Characteristics of Thin Films Prepared with Photochromic Thin Film Compositions Capable of Polymerization Photochromic characteristics of the thin films prepared in Examples 12–14 and Comparative Examples 12–13 were summarized in table 4.

TABLE 4

| Category | | Photochromic composition | Substituent of diarylethene | | Content (wt. %) | Thickness of film (μm) | $\lambda_{max}$ | Δ OD* (cm$^{-1}$) |
|---|---|---|---|---|---|---|---|---|
| Exam | 12 | Exam 8 | —H | (isoxazole-phenyl) | 10 | 12 | 539 | 259 |
| | 13 | Exam 9 | (isoxazole-phenyl) | (isoxazole-phenyl) | 10 | 15 | 545 | 280 |
| Comp. Exam. | 12 | Comp. Exam. 6 | —H | acetyl (COCH$_3$) | 10 | 18 | 533 | 231 |
| Exam. | 14 | Exam. 8 | —H | (isoxazole-phenyl) | 10 | 17 | 538 | 185 |
| Comp. Exam | 13 | Comp Exam 6 | —H | acetyl (COCH$_3$) | 10 | 12 | 540 | 180 |

Δ OD* is an amended value with the thickness of thin film for the difference between absorbance of $\lambda_{max}$ before and after UV irradiation.

As shown in Experimental Examples 1 and 2, the compositions of Examples 11–14 containing photochromic diarylethene compound PIMBTF6 provide superior photochromic effect to that of Comparative Example 1 containing BTF6 and Comparative Examples 2 and 6 containing AMBTF6. And further, photochromic effect was generally better with fluorinated diacrylate substrate than that with polycarbonate substrate.

Accordingly, diarylethene compounds having isoxazole group of the present invention provide excellent dispersability with polymers, especially fluorinated diacrylate monomer capable of photopolymerization, and photochromic effect, so that such compounds or composition containing the same can be highly useful in the preparation of optical recording materials, photo switch, photosensitive drum, recording elements, fiber and optical elements.

What is claimed is:

1. A photochromic diarylethene compound having isoxazole group expressed in the following formula (1), (I)

wherein $R^1$ is a direct bond; $R^2$ is a hydrogen atom, $(CR^4H)_nOH$ or $C_6(R5)_mH_1$; $R^3$ is selected from the group consisting of a hydrogen atom, phenylisoxazole, hydroxymethylisoxazole, acetyl, hydroxy, and phenyl; $R^4$ is hydrogen or $C_1$–$C_{10}$ alkyl; $R^5$ is chloro, nitro, bromo, or the same as $R^4$; X and Y are S; Z is methylene optionally substituted with fluoro or carbonyl; and n, m and l are an integer of 1 to 5.

2. A method for preparing the diarylethene compound of claim 1, comprising the steps:
(i) formylating diarylethene compound of formula (2);
(ii) reacting the formylated compound with NH$_2$OH.HCl and aqueous basic solution in series and reacting with N-chlorosuccinimide (NCS); and
(iii) reacting with acetylene compound substituted with R$^2$ in the presence of base catalyst, (2)

wherein R$^1$ is a direct bond; R$^3$ is selected from the group consisting of a hydrogen atom, phenylisoxazole, hydroxymethylisoxazole, acetyl, hydroxy, and phenyl; X and Y are S; and Z is methylene optionally substituted with a fluoro atom or carbonyl.

3. A compound selected from the group consisting of 1-(6'-(5-hydroxymethylisoxazol)-2'-methylbenzo[b]thiophen-3'-yl)-2-(2''-methylbenzo[b]thiophen-3'-yl)hexafluorocyclopentene, 1-(6'-(5-phenylisoxazol)-2'-methylbenzo[b]-thiophen-3'-yl)-2-(2''-methylbenzo[b]thiophen-3'-yl)hexafluorocyclopentene, and di(6'-phenylisoxazol-2'-methylbenzo[b]thiophen-3'-yl)hexafluorocyclopentene.

* * * * *